(12) United States Patent
Attawia et al.

(10) Patent No.: US 12,137,891 B2
(45) Date of Patent: Nov. 12, 2024

(54) INTERVERTEBRAL DISC PUNCTURE AND TREATMENT SYSTEM

(71) Applicant: DePuy Synthes Products, Inc., Raynham, MA (US)

(72) Inventors: Mohamed Attawia, Canton, MA (US); Cynthia Lee, Jamaica Plain, MA (US); Hassan Serhan, South Eason, MA (US); Michael O'Neil, West Barnstable, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/811,420

(22) Filed: Jul. 8, 2022

(65) Prior Publication Data
US 2022/0338854 A1 Oct. 27, 2022

Related U.S. Application Data (63) Continuation of application No. 16/511,470, filed on Jul. 15, 2019, now Pat. No. 11,389,148, which is a continuation of application No. 15/061,786, filed on Mar. 4, 2016, now Pat. No. 10,349,928, which is a continuation of application No. 11/422,222, filed on Jun. 5, 2006, now abandoned.

(51) Int. Cl.
| | | |
|---|---|---|
| *A61B 17/02* | (2006.01) | |
| *A61B 17/34* | (2006.01) | |
| *A61F 2/46* | (2006.01) | |
| *A61B 17/00* | (2006.01) | |
| *A61F 2/44* | (2006.01) | |

(52) U.S. Cl.
CPC ...... *A61B 17/0218* (2013.01); *A61B 17/3415* (2013.01); *A61F 2/4611* (2013.01); *A61B 2017/00026* (2013.01); *A61B 2017/00039* (2013.01); *A61B 2017/00261* (2013.01); *A61B 2017/0262* (2013.01); *A61F 2002/444* (2013.01); *A61F 2002/4627* (2013.01)

(58) Field of Classification Search
CPC ............ A61B 17/0218; A61B 17/3415; A61B 2017/00026; A61B 2017/00039; A61B 2017/00261; A61F 2/4611
USPC ........................................................ 604/264
See application file for complete search history.

(56) References Cited

U.S. PATENT DOCUMENTS

| | | | |
|---|---|---|---|
| 4,270,535 A | 6/1981 | Bogue et al. | |
| 4,791,937 A | 12/1988 | Wang | |
| 5,088,982 A | 2/1992 | Ryan | |
| 5,827,305 A | 10/1998 | Gordon | |
| 5,871,470 A * | 2/1999 | McWha | A61B 17/3401 604/158 |

(Continued)

OTHER PUBLICATIONS

Office Action dated Nov. 12, 2021, in U.S. Appl. No. 16/511,470, filed Jul. 15, 2019.

(Continued)

*Primary Examiner* — Phillip A Gray
(74) *Attorney, Agent, or Firm* — Dunlap Codding, P.C.

(57) ABSTRACT

A pre-assembled, telescoping elongate system comprising an outer elongate member surrounding a finer gauge inner elongate member which, after percutaneous penetration by the outer elongate element, extends to penetrate an intervertebral disc into which a sensing element and/or an injectable may be delivered.

19 Claims, 11 Drawing Sheets

(56) References Cited

U.S. PATENT DOCUMENTS

| | | | |
|---|---|---|---|
| 6,066,122 | A | 5/2000 | Fisher |
| 6,245,044 | B1 | 6/2001 | Daw et al. |
| 6,497,686 | B1 | 12/2002 | Adams et al. |
| 6,613,017 | B1 * | 9/2003 | Mickley ............ A61M 25/0084 604/117 |
| 6,695,822 | B2 | 2/2004 | Adams et al. |
| 7,799,833 | B2 | 9/2010 | Boyd |
| 2002/0019626 | A1 | 2/2002 | Sharkey et al. |
| 2004/0229878 | A1 | 11/2004 | DiMauro et al. |
| 2005/0182454 | A1 | 8/2005 | Gharib et al. |
| 2005/0234425 | A1 | 10/2005 | Miller et al. |

OTHER PUBLICATIONS

Response to Office Action dated Mar. 2, 2022, in U.S. Appl. No. 16/511,470, filed Jul. 15, 2019.
Notice of Allowance dated Mar. 24, 2022, in U.S. Appl. No. 16/511,470, filed Jul. 15, 2019.

* cited by examiner

INTERVERTEBRAL DISC PUNCTURE AND TREATMENT SYSTEM

CROSS REFERENCE TO RELATED APPLICATIONS/INCORPORATION BY REFERENCE STATEMENT

The present application is continuation of U.S. Ser. No. 16/511,470, filed Jul. 15, 2019; which is a continuation of the patent application identified by U.S. Ser. No. 15/061,786, filed Mar. 4, 2016, now U.S. Pat. No. 10,349,928, issued Jul. 16, 2019; which is a continuation of U.S. Ser. No. 11/422,222, filed Jun. 5, 2006, now abandoned. The entire contents of each patent/patent application listed above are hereby incorporated herein by reference.

BACKGROUND

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases ("MMPs"). These cytokines and MMPs help regulate the metabolism of the nucleus pulposus cells.

In some instances of disc degeneration disease (DDD), gradual degeneration of the intervertebral disc is caused by mechanical instabilities in other portions of the spine. In these instances, increased loads and pressures on the nucleus pulposus cause the cells to emit larger than normal amounts of the above-mentioned cytokines. In other instances of DDD, genetic factors, such as programmed cell death, or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins.

As DDD progresses, the toxic levels of the cytokines present in the nucleus pulposus begin to degrade the extracellular matrix. In particular, the MMPs (under mediation by the cytokines) begin cleaving the water-retaining portions of the proteoglycans, thereby reducing their water-retaining capabilities. This degradation leads to a less flexible nucleus pulposus, and so changes the load pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

US Published Patent Application 2004/0229878 discloses a procedure for the intradiscal administration of therapeutics, wherein an outer needle and an inner stylet are advanced to the annulus fibrosus, the stylet is withdrawn and replaced with an inner needle attached to a syringe, and the inner needle is advanced to the nucleus pulposus for injection of the therapeutic into the nucleus pulposus.

In other approaches, a single, fine gauge needle is used to penetrate the skin and musculature approaching the intervertebral disc. However, the drawbacks of this approach include the need for a relatively sturdy needle and an increase in the risk of infection to the disc (due to the fact that the needle that pierces the skin is also the needle that enters the disc).

To reduce the risk of infection and subsequent discitis that may result from percutaneous procedures, one common practice is to use a double needle approach in which a larger gauge needle is used to penetrate the skin and a second finer, gauge needle is passed through the first needle and into the intervertebral disc. However, this approach requires two separate needles and manual insertion of the second needle inside of the first.

Some needle systems developed for use outside of the disc area have dual needle designs. For example, in needle systems unrelated to intradiscal delivery of therapeutics, various needle systems and procedures are employed for aspirating body fluids, and some of these employ concentric multi-gauge needles. Various access needle systems designed to treat ailing tissue are made to allow a second device to pass through an outer access needle. Various extendable/retractable needle systems exist as safety devices to prevent user injury by needle sticks.

U.S. Pat. Nos. 5,871,470 and 6,245,044 disclose a set of interlocking concentric epidural-spinal needles for delivery of medicaments into the epidural and subarachnoid spaces. However, these systems contain two separate needles that the user must assemble. Neither system is pre-assembled.

U.S. Pat. Nos. 6,497,686 and 6,695,822 disclose a method and device for performing sterile endoluminal procedures using a needle system that includes two concentric needles. However, these systems do not allow for aspiration of the medicament into an attached syringe. Moreover, the distal portion of the device is designed to remain in place after the procedure is completed.

DETAILED DESCRIPTION

Certain non-limiting embodiments of the present disclosure provide simple and safe percutaneous access to the intervertebral disc for intradiscal delivery of therapeutic agents to the disc.

The present inventors have developed a pre-assembled, telescoping needle system comprising an outer needle surrounding a finer gauge inner needle. After percutaneous penetration by the outer needle and its advance to the annulus fibrosus, the inner needle is moved distally to extend past the outer needle and penetrate the intervertebral disc. A therapeutic agent may then be delivered from a syringe through the inner needle and into the nucleus pulposus.

The needle system of the present disclosure provides a number of advantages over the conventional intradiscal needle systems.

First, the needle system is pre-assembled. This enables both ease of use by the clinician and a reduced diameter of the inner (injection) needle, as it is supported by the outer needle during its insertion at the disc site.

Second, there is a reduced risk of discitis (intradiscal infection). The inner injection needle is shielded by the outer cannula from contact or exposure to the operative environment, skin and soft inner tissues. This reduced exposure yields a reduced infection potential.

Third, the present disclosure provides a controlled discal injection depth. The present disclosure allows for placement of the tip of the outer needle at or upon the outer rim of the annulus fibrosus, and subsequent advancement of the inner needle into the disc space. Controlled and monitored advancement of the inner needle into the disc space allows for pre-determination or measured determination of intradiscal injection depths and associated location.

Therefore, in accordance with the present disclosure, there is provided a method of delivering a therapeutic agent to an intervertebral disc having an annulus fibrous and a nucleus pulposus, comprising the steps of:
a) providing a therapeutic delivery system, comprising:
  i) an outer needle having a distal end, and
  ii) an inner needle received within the outer needle and having a distal end,
b) inserting the outer needle into the patient at a location dorsal of the intervertebral disc,
c) advancing the outer needle to abut the annulus fibrosus, and then
d) advancing only the inner needle into the nucleus pulposus.

The present disclosure comprises a dual needle intradiscal device comprising a larger gauge outer needle and a smaller gauge inner needle. In certain particular (but non-limiting) embodiments, the needles are sized for intradiscal injection through a percutaneous approach.

The outer needle serves as the access needle, as it functions to pierce and penetrate the patient's skin and muscle up to the annulus fibrosus. Further, it functions as a shield for the inner needle prior to its entry into the disc, thereby minimizing the chances of the inner needle infecting the disc and subsequent discitis. In certain particular (but non-limiting) embodiments, the outer needle has a sufficient stiffness and length to penetrate the skin and underlying muscle, and is, in certain particular (but non-limiting) embodiments, between 10 gauge and 20 gauge in bore diameter and between 8 cm and 20 cm in length.

The inner needle has a length sufficient to penetrate the annulus fibrosus region of the disc, and is typically between 4 cm and 10 cm longer than the outer needle. In order to minimize damage to the intervertebral disc, the inner needle should be a fine gauge needle, such as (but not limited to) between 22 gauge and 32 gauge. The proximal end of the inner needle can attach to a standard syringe.

In certain particular (but non-limiting) embodiments, the position of the outer needle can be advanced and then fixed at various positions along the axis of the inner needle according to the needs of the clinician. In certain particular (but non-limiting) embodiments, this is accomplished with a locking mechanism.

For example, in one embodiment, the inner needle is first set in a first locked position to extend about 0.5 cm to 1 cm beyond the outer needle so that medicament can be aspirated proximally into the syringe through the distal end of the inner needle. Once the medicament has been aspirated into the syringe, the locking mechanism can be unlocked and the inner needle retracted and fixed at a new position such it sits 0.5 cm to 1 cm proximal to the distal end of the outer needle. In this second locked position, the needle system can be inserted through the patient's skin. When the outer needle has penetrated to a sufficient depth (such as up to the annulus fibrosus), the locking mechanism can again be unlocked and the inner needle can slide distally relative to the outer needle and penetrate the disc.

In some particular (but non-limiting) embodiments, the locking mechanism is provided via a ball detent mechanism. Now referring to FIGS. 1A and 1B, in some embodiments, there is provided a needle system 1 for intradiscal delivery of a therapeutic agent, comprising:
a) an outer needle 3 having an outer surface 5 having a transverse throughhole 7, and a detent 9 provided in the throughhole, the detent having a projection 11 extending inwardly, and
b) an inner needle 13 having an outer surface 15 having a plurality of axially spaced grooves 17, wherein the projection of the detent is shaped to be received in the plurality of axially spaced grooves.

In some embodiments thereof, the outer surface of the outer needle has a hole therein into which a pushbutton detent is releasably provided. The outer surface of the inner needle contains a plurality of grooves spaced at predetermined intervals. When the push button of the outer needle is engaged with groove of the inner needle, the needle system is locked and the relative axial positions of the two needles are fixed. When the push button of the outer needle is disengaged from a groove of the inner needle, the system is unlocked and the inner needle may be moved forward or backward relative to the outer needle (or vice versa). FIG. 2 shows the distal movement of the inner needle 13 by a single stop interval as compared to its position in FIG. 1A.

In some particular (but non-limiting) embodiments, the locking mechanism is provided via a pair of mating threads. In these embodiments, the inner needle can be threadably connected to the outer needle and advanced to a desired depth in the disc by rotation of the inner needle within the outer needle. Now referring to FIGS. 3A and 3B, in some embodiments, there is provided a needle system 21 for intradiscal delivery of a therapeutic agent, comprising:
a) an outer needle 23 having an inner surface 25 having a first thread 27, and b) an inner needle 31 having an outer surface 33 having a second thread 35, wherein the first thread is adapted to mate with the second thread.

Figure 3A:
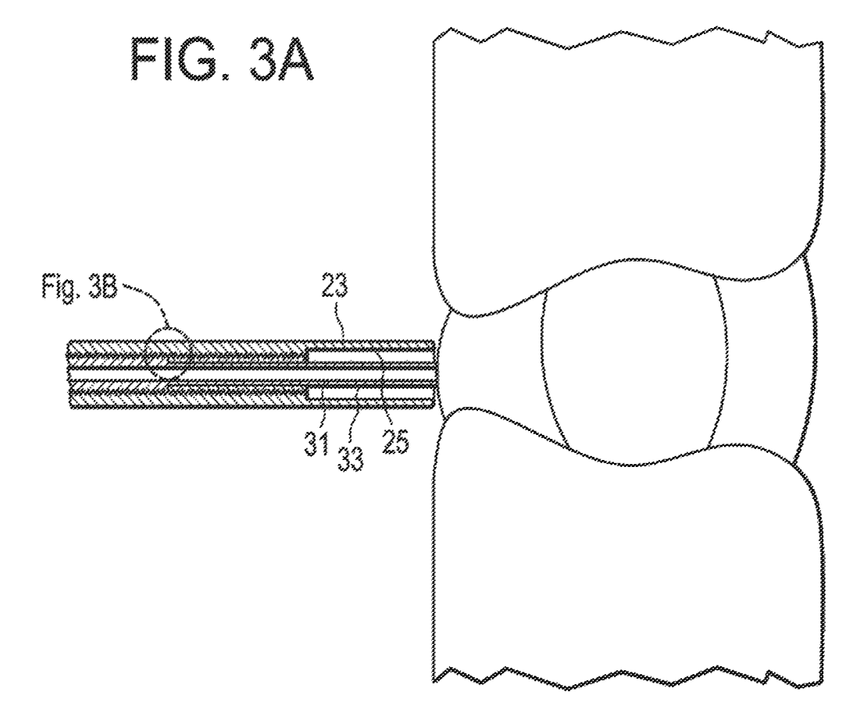
FIG. 3A discloses a cross section of the needle system of the present disclosure having a threaded locking mechanism, prior to its deployment into an intervertebral disc.
Figure 3B:
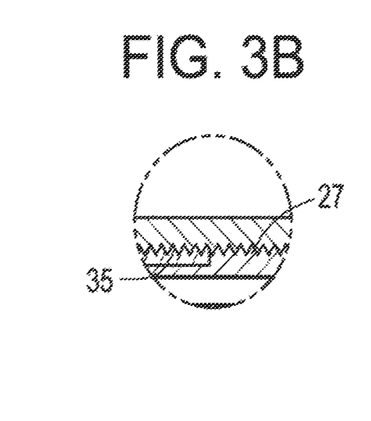
FIG. 3B is an enlarged cross section of the locking mechanism of FIG. 3A.

When one of the needles is rotated in respect to the other needle, the relative rotation of the engaged threads is such that axial movement of the inner needle is accomplished.

Figure 4:
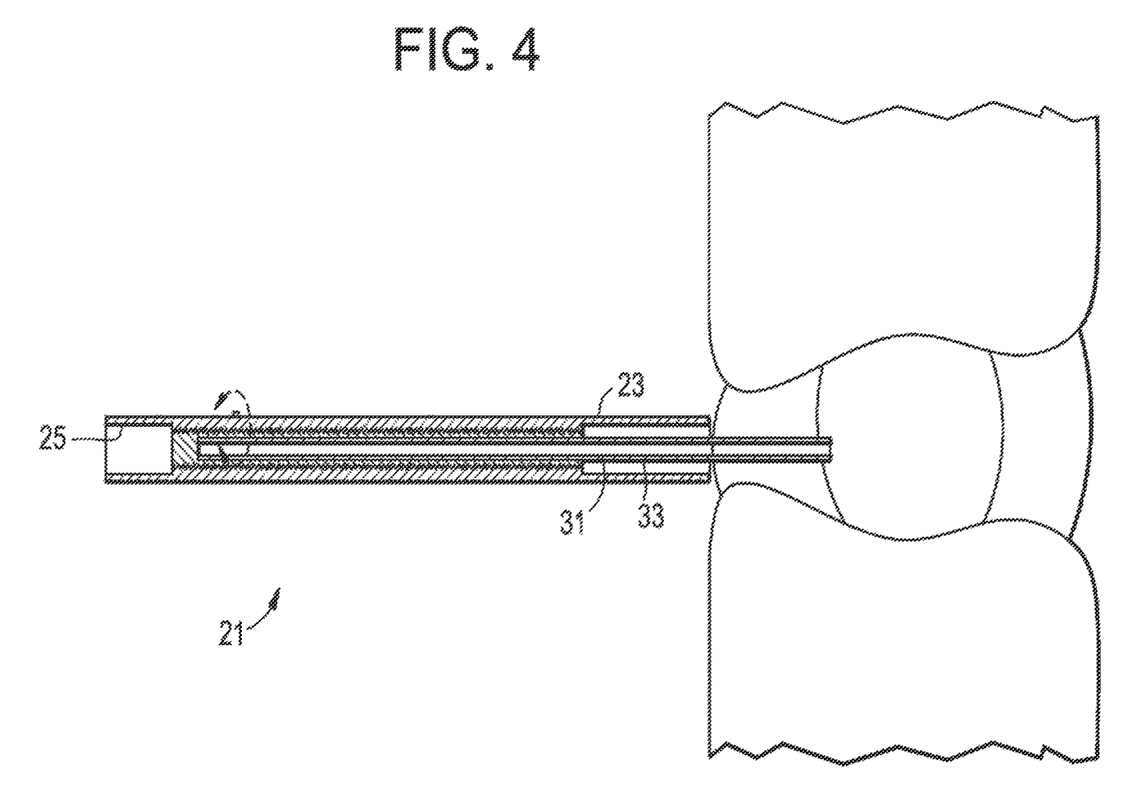
FIG. 4 discloses a cross section of the needle system of FIG. 3A, after its deployment into an intervertebral disc.

FIG. 4 shows the distal movement of the inner needle produced by relative rotation of the threads, as compared to its position in FIG. 3A.

Figure 5A:
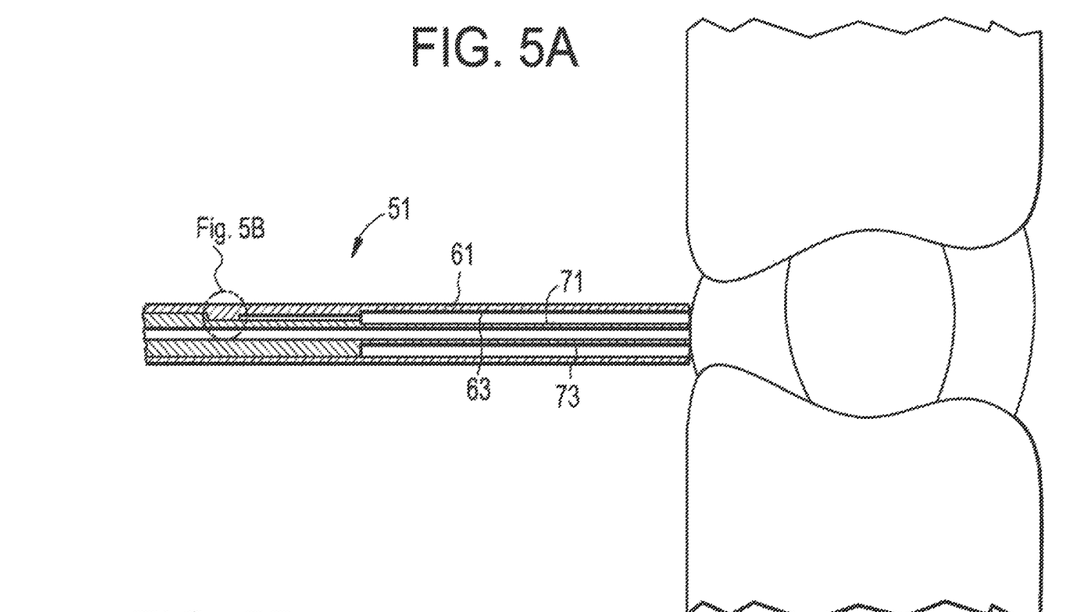
FIG. 5A discloses a cross section of the needle system of the present disclosure having a keyed locking mechanism, prior to its deployment into an intervertebral disc.
Figure 5B:
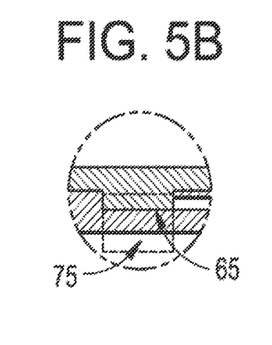
FIG. 5B is an enlarged cross section of the locking mechanism of FIG. 5A.
Figure 5C:
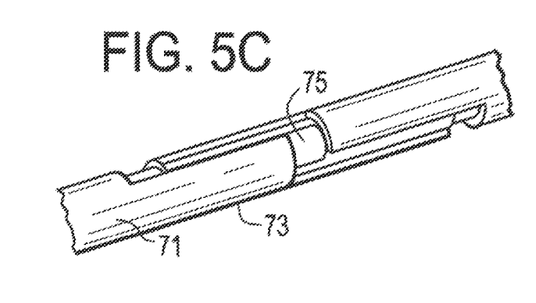
FIG. 5C is a perspective view of the inner needle of FIG. 5A having a channel herein.

Now referring to FIG. 5A-5C, in some embodiments, the stops are provided by a keyed mechanism. In FIGS. 5A-5C, there is provided a needle system 51 for intradiscal delivery of a therapeutic agent, comprising:

a) an outer needle 61 having an inner surface 63 having a tab 65 extending therefrom, and b) an inner needle 71 having an outer surface 73 having a channel 75 therein, wherein the tab is received in the channel.

In certain non-limiting embodiments thereof, the inner diameter of the outer needle has a tab extending therefrom, while the outer diameter of the inner needle has a channel therein, wherein the channel has alternating axial and lateral portions defining a plurality of stop intervals. In use, the clinician moves the inner needle distally until the tab of the outer needle abuts the lateral portion of the inner needle. If the clinician desires to move the inner needle distally again, the clinician rotates the inner needle so that the tab moves along the lateral portion of the channel and enters the next axial portion of the channel. The clinician then moves the inner needle axially once again, with the channel of the inner needle being guided by the tab, until the tab of the outer needle abuts the next lateral portion of the inner needle.

Figure 6:
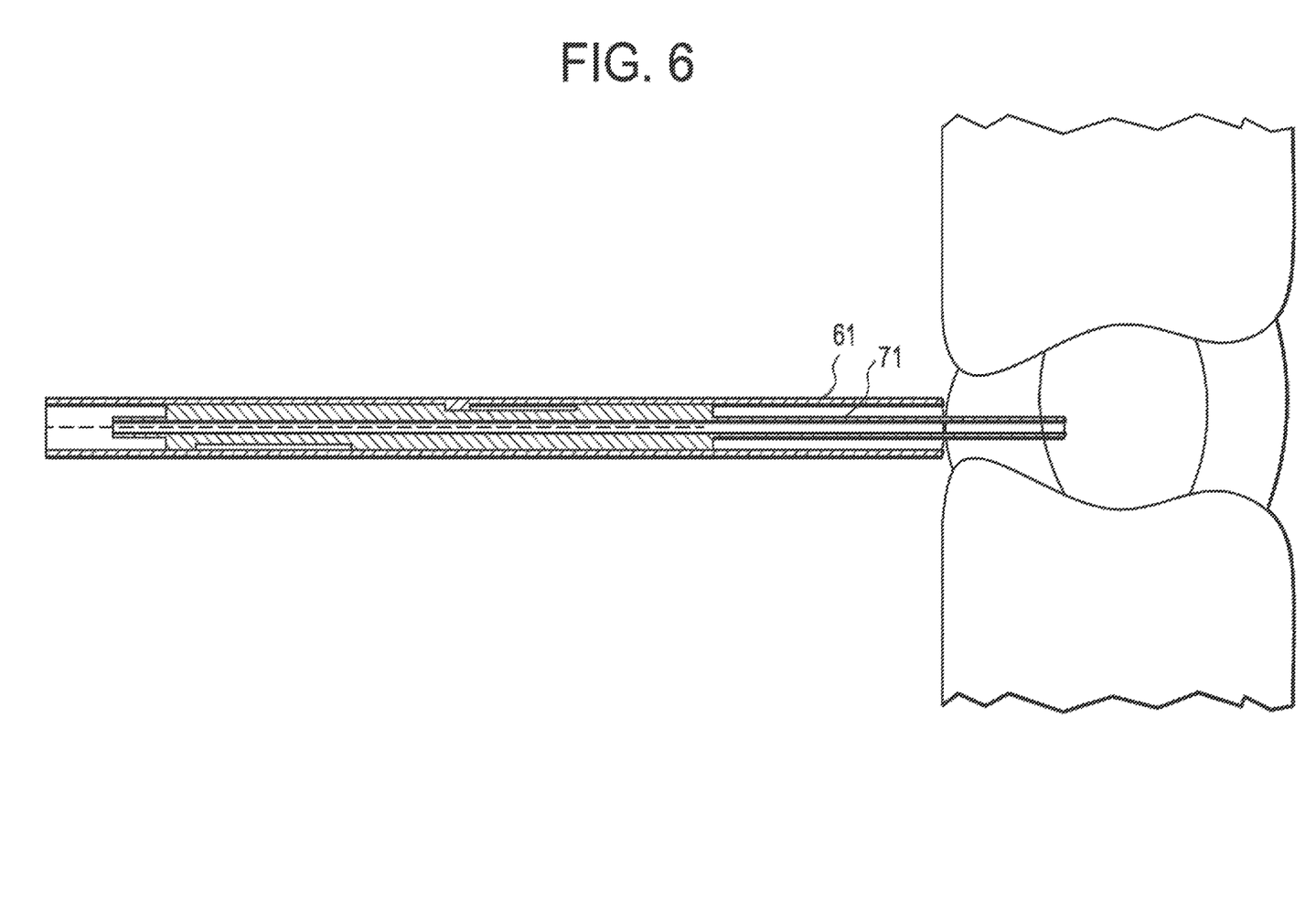
FIG. 6 discloses a cross section of the needle system of FIG. 5A, after its deployment into an intervertebral disc.

FIG. 6 shows the distal movement of the inner needle produced by movement of the tab in the channel, as compared to its position in FIG. 5A.

In other embodiments using a keyed locking mechanism, the inner surface of the outer needle has the channel and the outer surface of the inner needle has the tab. In one particular (but non-limiting) embodiment, the keyed locking mechanism includes a simple twist-lock mechanism such that in two predetermined rotational positions (e.g., 0° and either 45°, 90°, 180°, or 270°), the outer needle can slide relative to the inner needle.

Figures 1A, 1B:
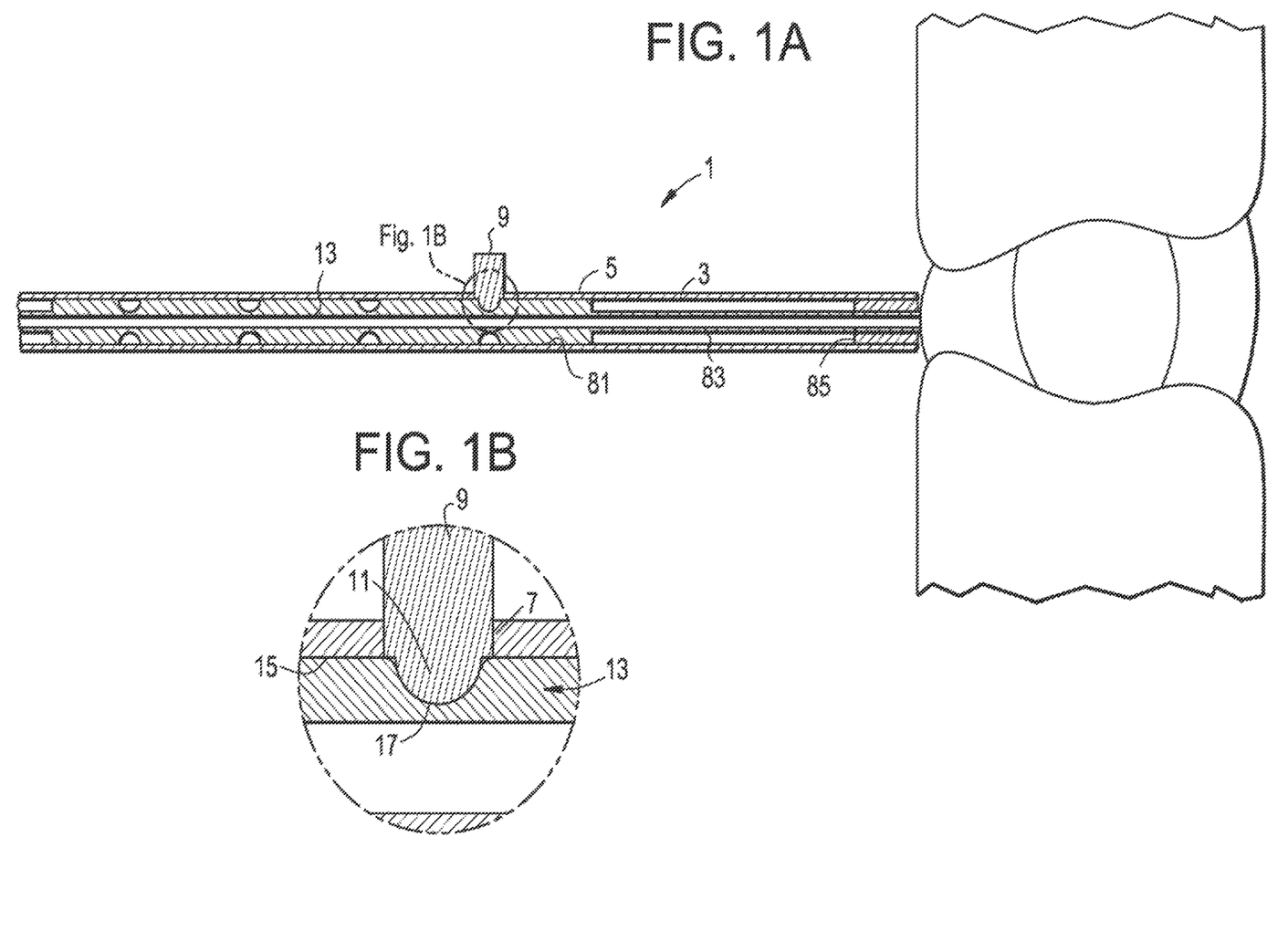
FIG. 1A discloses a cross section of the needle system of the present disclosure having a ball detent locking mechanism, prior to its deployment into an intervertebral disc.
FIG. 1B is an enlarged cross section of the locking mechanism of FIG. 1A.
Figure 2:
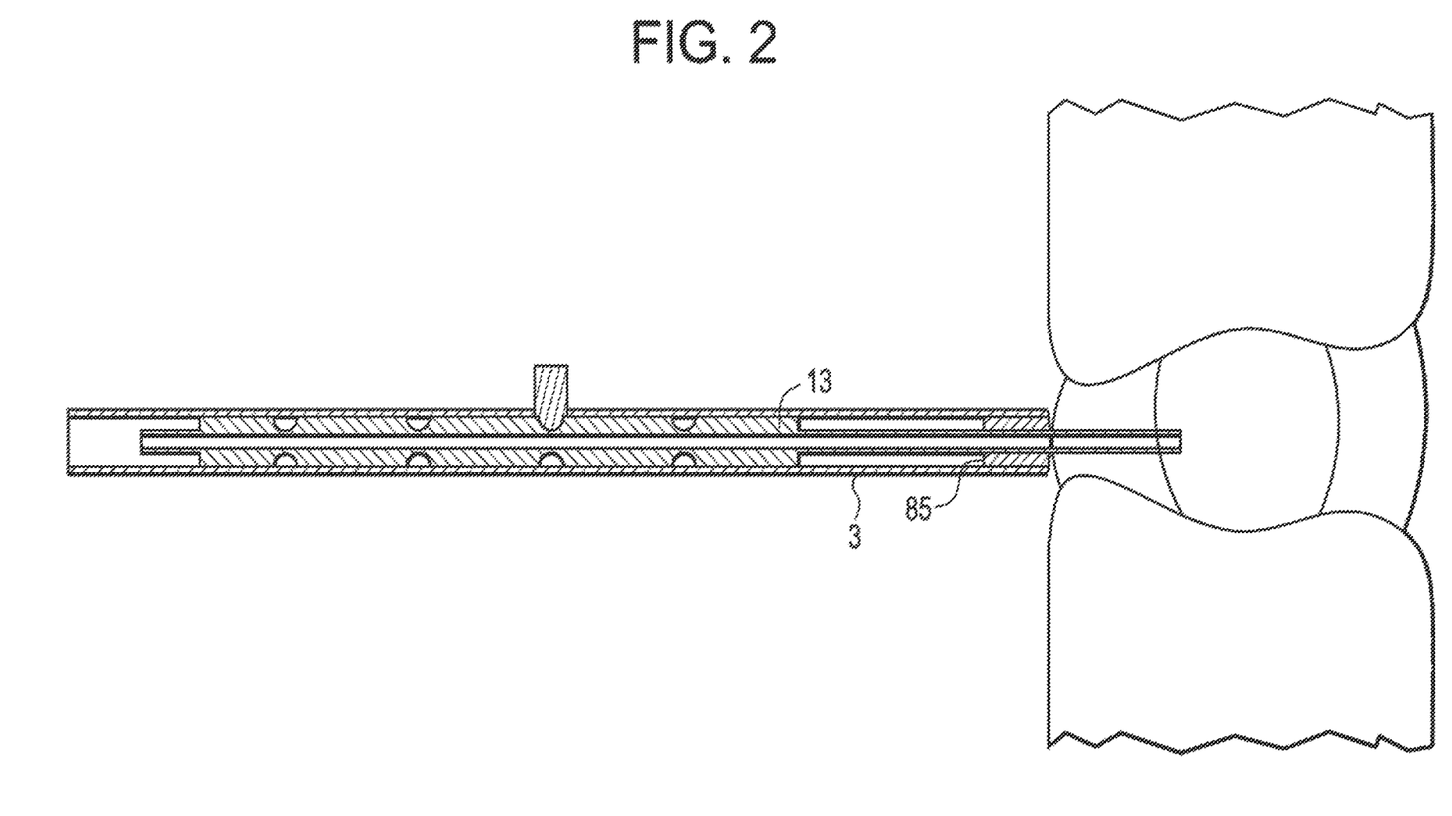
FIG. 2 discloses a cross section of the needle system of FIG. 1A, after its deployment into an intervertebral disc.

In some embodiments using a locking mechanism, and now referring to FIG. 1A, the inner needle has a first proximal outer diameter 81 and a second distal outer diameter 83, wherein the first proximal outer diameter is greater than the second distal outer diameter. This embodiment minimizes the diameter of the portion of the needle that penetrates the annulus fibrosus, thereby reducing injury to the annulus fibrosus. In some embodiments thereof, the system further comprises an annular plug 85 disposed within the distal end of the outer needle and adapted to fit between the inner and outer needles. The annular plug prevents fluid from entering the bore of the outer needle when the inner needle has a reduced diameter and provides a guide for the distal advance of the inner needle. In this non-limiting embodiment, the first proximal outer diameter is preferably (but not by way of limitation) sized to be slightly less than the inner diameter of the outer needle, so that the locking mechanism (whether it be a ball detent mechanism, a pair of threads, or a keyed mechanism) possesses a snug fit.

In some embodiments, after the medicament is administered, the locking mechanism can be re-engaged and the two needles can be removed together from the patient. In other embodiments, after the medicament is administered, the locking mechanism remains disengaged and the two needles are removed independently.

In some embodiments wherein only the inner needle is removed, a second needle can be inserted through the same outer needle. In some embodiments thereof, this second inner needle may be a standard needle that does not lock to the outer needle. In other embodiments thereof, this second inner needle may comprise a locking feature that is engageable with a locking feature of the outer needle.

In some embodiments, depth markings can be provided to allow the clinician to measure the depth of discal entry and location of the treatment within the nucleus pulposus, and thereby control the depth of discal entry and location of the treatment within the nucleus pulposus.

The needle system of the present disclosure can be suitably used to inject therapeutic agents into intravertebral disc and synovial joints (such as facet joints, hip joints and knee joints). It may be used in the aspiration of bone marrow or for biopsy procedures.

In some embodiments, the therapeutic materials disclosed in US Published Patent Application 2004/0229878, which is incorporated by reference in its entirety, are injected into the disc.

Figure 7A:
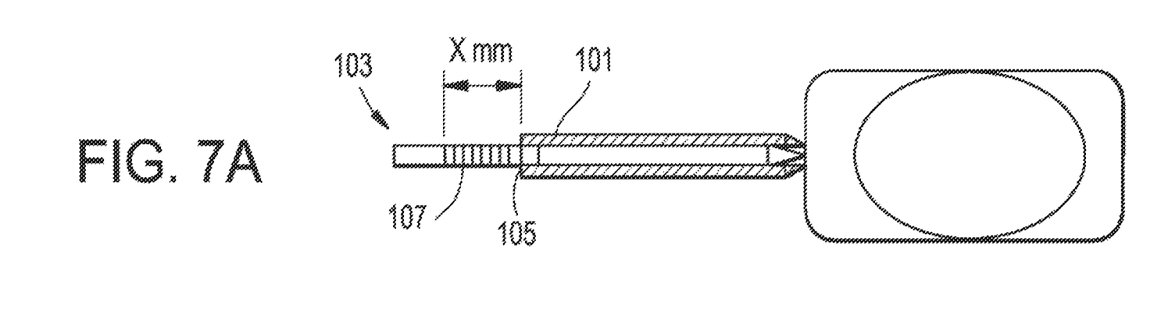
FIGS. 7A and 7B disclose cross sections of generalized needle systems of the present disclosure.
Figure 7B:
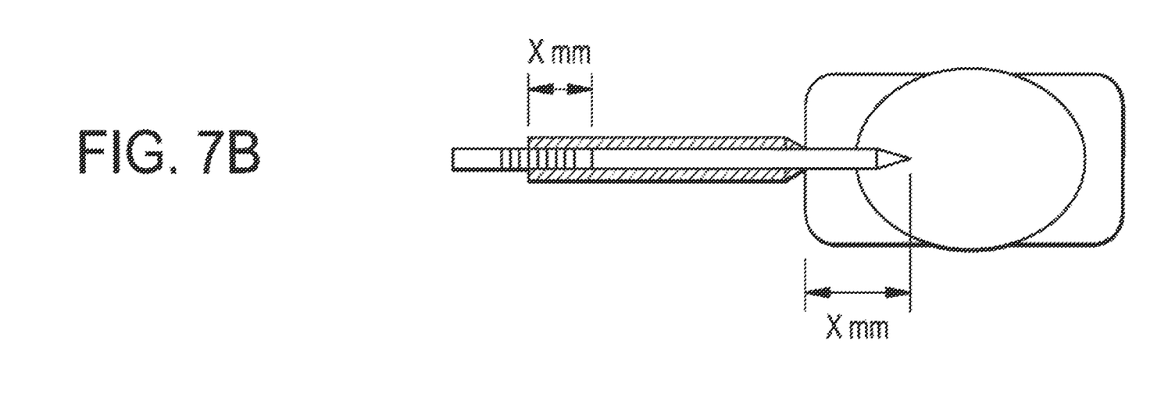

FIGS. 7A and 7B depict the general concept of the Intervertebral Puncture and Treatment System in its respective pre-insertion and post-insertion modes. During pre-insertion, and now referring to FIG. 7A, the tips of the outer cannula 101 and inner needle 103 are aligned and advanced until disc contact is observed. In some embodiments thereof, the outer cannula is about 18 gauge RW, with a 0.033 inch ID and a 0.050 inch OD, while the inner delivery needle is about 22 gauge RW, with a 0.016 inch ID and a 0.028 inch OD. Also shown is a generalized representation of a depth control means 105 (that is enabled in subsequent figures by threaded advancement and keyway stops). Depth control markings 107 correspond to the insertion depth (x mm) into the disc following contact with the annular wall, as can be seen in the post-insertion image FIG. 7B.

Figure 8A:
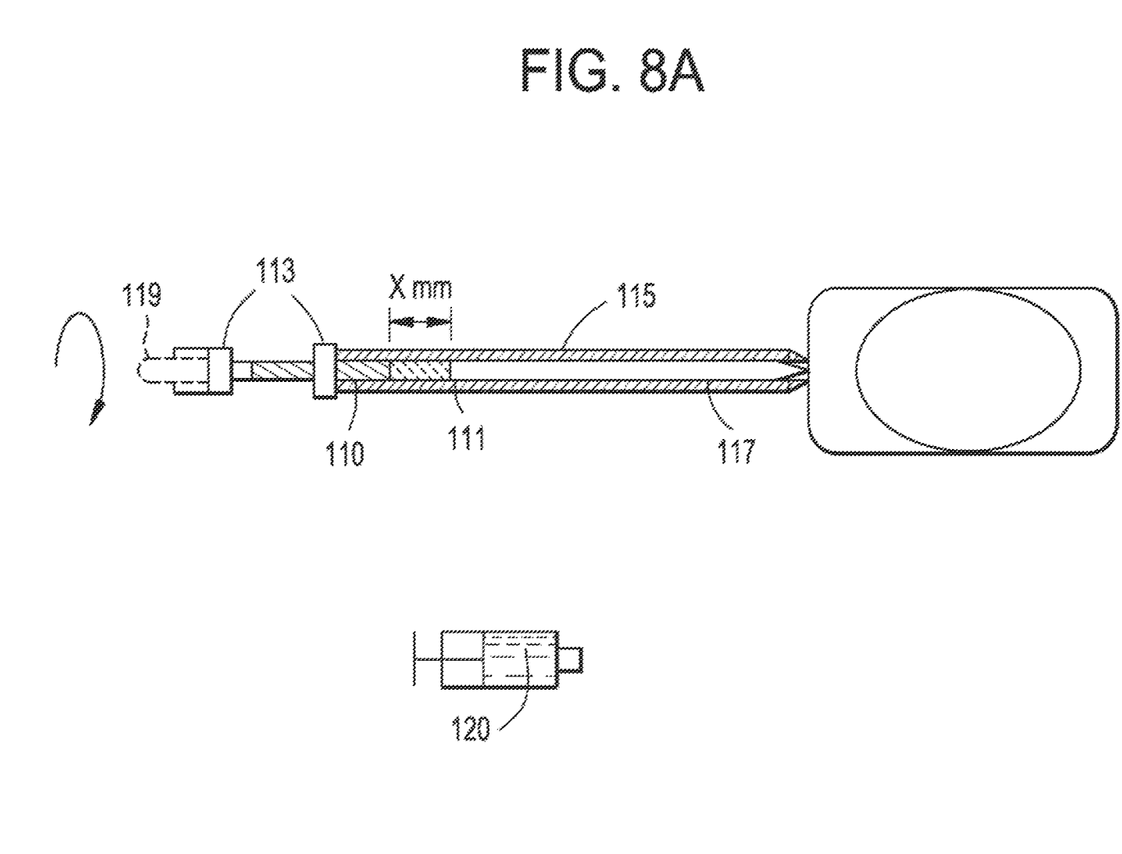
FIGS. 8A and 8B disclose cross sections of needle systems of the present disclosure having threaded advancement.

Now referring to FIG. 8A, there is provided a more detailed embodiment depicted device orientation pre-insertion into the disc. This device has a threaded advancement means 110 and a positive depth stop 111 (as shown by ghost threads) at an insertion depth of x mm. Handles 113 are provided on each of the outer cannula 115 and inner needle 117 to assist in threading the inner needle into the outer cannula. Also shown in this FIG. 8A is the treatment attachment location 119 (which may be, for example, a luer slip, luer lock, or injection cap) at which the device is attached to a treatment container 120 (which may be, for example, a syringe, vial, bag, or pouch).

Figure 8B:
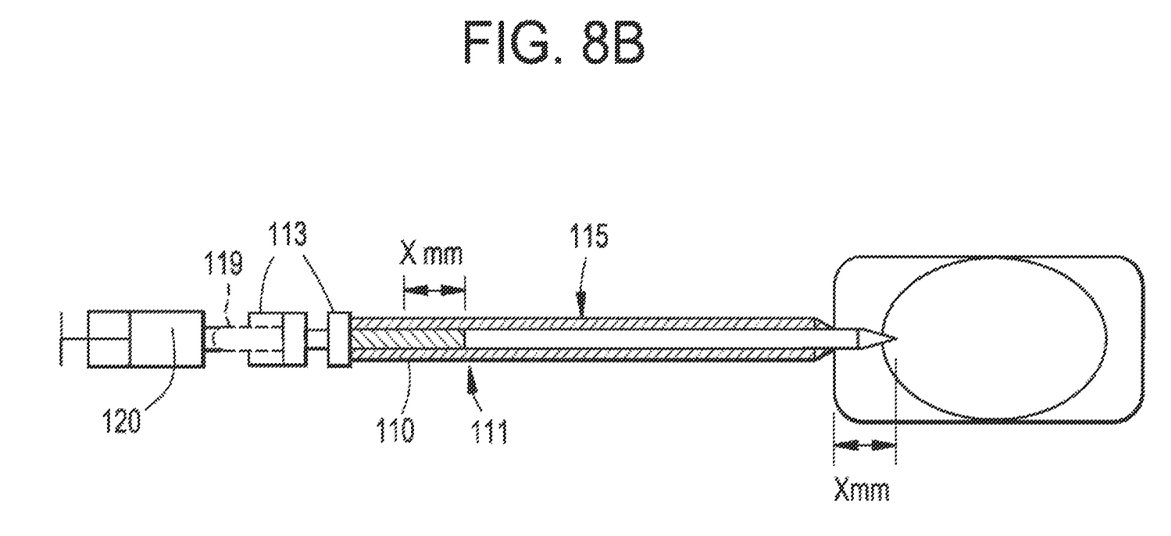

FIG. 8B discloses the threaded advancement device of FIG. 8A following insertion into the disc. In this case, threaded advancement of the inner needle has been stopped by the positive depth stop 111 (provided by the end of the threads) at a predetermined depth of x mm. Also shown in this figure are handles 113, outer cannula 115, inner needle 117, and the treatment container 120 attached to the inner needle 117 at treatment attachment location 119 for dispensing at desired depth.

Figure 9A:
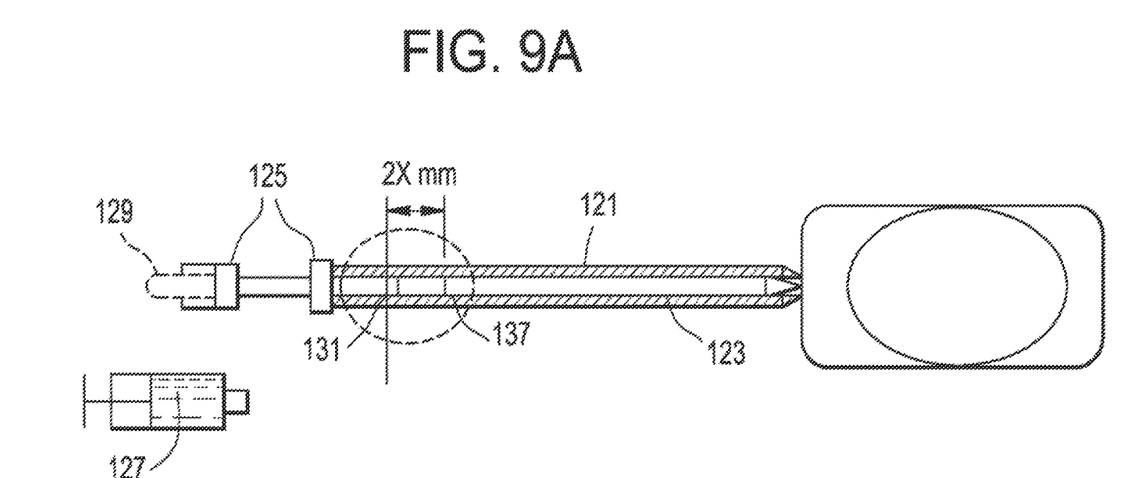
FIGS. 9A-9D disclose cross sections of needle systems of the present disclosure having keyed advancement.
Figure 9B:
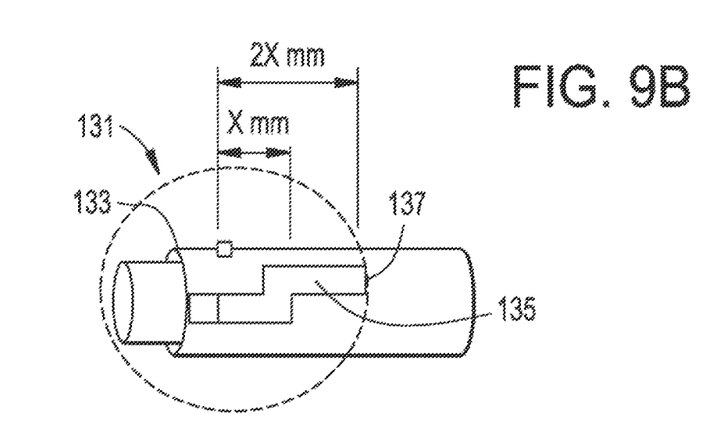

Now referring to FIGS. 9A and 9B, there is provided a device having an outer cannula 121, an inner needle 123, advancement handles 125, a treatment container 127 attached to the inner needle at a treatment location 129, and keyed advancement means 131 in its pre-insertion configuration. The key 133 is located on either the outer and inner needle (shown here on the inner needle as a protrusion) and is disposed within keyway 135. The distance between the key and the keyway stop 137 will control the depth of intradiscal insertion (2x mm) following contact with the annulus.

Figure 9C:
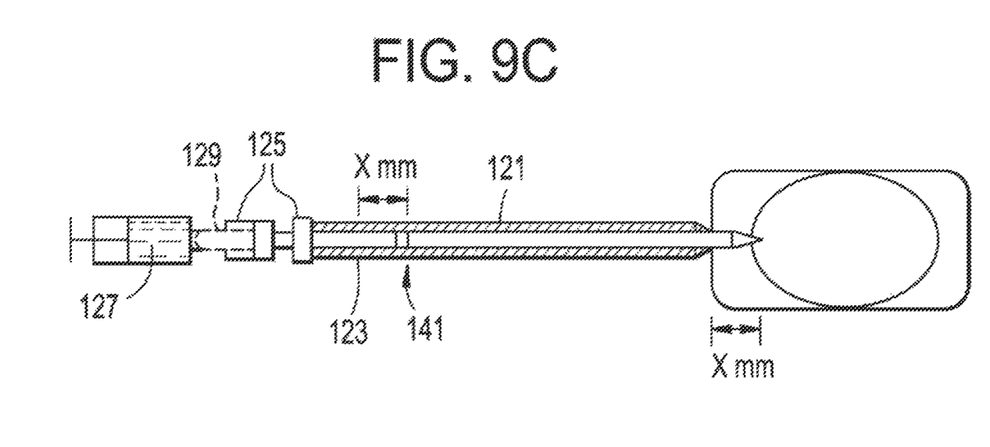
Figure 9D:
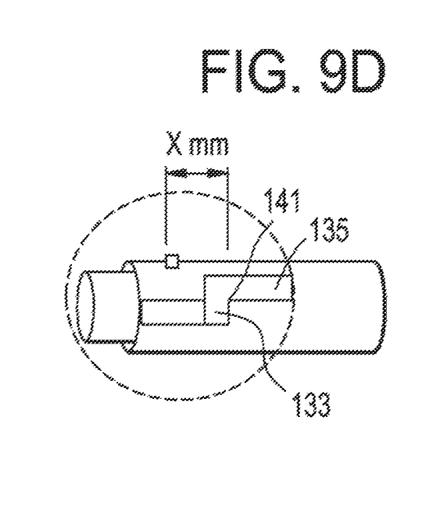

Now referring to FIGS. 9C and 9D, there is provided the device of FIGS. 9A and 9B in its post-insertion configuration. In this case, inner needle 123 and its accompanying key 133 have been advanced until the keyway stop is contacted (x mm). Additional advancement of the inner needle (for example, 2x mm) may be obtained by rotating the inner needle (for example, 90 degrees) and applying an advancement force until the second key way stop is contacted.

Example

This non-limiting prophetic example describes how to transdiscally administer a formulation comprising a therapeutic agent and saline into a nucleus pulposus of a degenerating disc.

First, a clinician uses a diagnostic test to verify that a particular disc within a patient has high levels of a particular pro-inflammatory cytokine.

Next, the clinician provides a local anesthetic (such as 5 ml lidocaine) to the region dorsal of the disc of concern to reduce subcutaneous pain.

Next, the clinician punctures the skin of the patient dorsal the disc of concern with a relatively large (e.g., 18-19 gauge) needle having a smaller gauge needle contained therein, and advances the needle through subcutaneous fat and dorsal sacrolumbar ligament and muscles to the outer edge of the intervertebral disc. The proximal end opening of the smaller needle is fluidly connected to a syringe. The barrel of the syringe contains the formulation of the present disclosure. The formulation contains REMICADE® infliximab, and has an infliximab concentration of between about 30 mg/ml and about 60 mg/ml.

Next, the physician advances the smaller needle coaxially through the larger needle and past the distal end of the larger needle, thereby puncturing the annulus fibrosus. The smaller needle is then further advanced into the center of the nucleus pulposus. Finally, the clinician depresses the plunger of the syringe, thereby injecting between about 0.1 and 1 ml of the formulation into the nucleus pulposus.

What is claimed is:

1. A preassembled elongate device, comprising: an outer tube having a substantially smooth outer surface, an inner surface defining a bore within the outer tube, an open distal end having an annular edge, and a proximal end, the outer tube having a sufficient stiffness and length to penetrate skin and muscle, and wherein the annular edge of the open distal end lies in a plane perpendicular to a longitudinal axis of the outer tube, whereby the annular edge is configured to abut an outer rim of an annulus fibrosus of an intervertebral disc so that the outer tube does not penetrate the annulus fibrosis; an inner elongate member housed within the bore of the outer tube, the inner elongate member having an outer surface, an inner surface defining a bore within the inner elongate member, an open distal end having an annular edge, and a proximal end, wherein the inner elongate member is slidably engaged by the outer tube such that the distal end of the inner elongate member can extend beyond the distal end of the outer tube whereby the inner elongate member has a retracted position and an extended position in relation to the outer tube, and wherein the annular edge of the distal end of the inner elongate member is configured to penetrate the annulus fibrosus and project into a nucleus pulposus of the intervertebral disc when in the extended position; a locking mechanism configured to provide releasable frictional engagement between the outer tube and the inner elongate member, wherein the locking mechanism controls slidable movement of the inner elongate member relative to the outer tube and thereby substantially prevents movement of the inner elongate member relative to the outer tube when the locking mechanism is engaged and allows the distal end of the inner elongate member to extend beyond the distal end of the outer tube when the locking mechanism is disengaged; further comprising an annular plug disposed within the distal end of the outer tube and adapted to fit between the outer tube and the inner elongate member, wherein the annular plug forms a seal that prevents fluid from entering a distal end of the bore of the outer tube.

2. The preassembled elongate device of claim 1, wherein at least one of:
    the outer tube has a bore diameter in a range of from about 10 gauge to about 20 gauge and a length in a range of from about 8 cm to about 20 cm;
    the inner elongate member has a bore diameter in a range of from about 22 gauge to about 32 gauge and a length in a range of from about 12 cm to about 30 cm; and
    the inner elongate member has a length that is about 4 cm to about 10 cm longer than a length of the outer tube.

3. The preassembled elongate device of claim 1, wherein the proximal end of the inner elongate member is configured for attachment of a treatment container thereto whereby the treatment container is in fluidic communication with the inner elongate member.

4. The preassembled elongate device of claim 1, wherein in the retracted position, the distal end of the inner elongate member is disposed within the outer tube at a position in a range of from about 0.5 cm to about 1 cm proximal to the distal end of the outer tube.

5. The preassembled elongate device of claim 1, wherein in the extended position, the distal end of the inner elongate member is configured to extend beyond the outer tube up to a length in a range of from about 0.5 cm to about 1 cm.

6. The preassembled elongate device of claim 1, wherein at least a portion of the outer surface of the inner elongate member has a plurality of depth markings thereon.

7. The preassembled elongate device of claim 1, wherein the locking mechanism comprises:
    at least one projection that extends from the inner surface of the outer tube; and
    a plurality of axially spaced indentations disposed on the outer surface of the inner elongate member, wherein each of the axially spaced indentations is shaped to receive at least a portion of the at least one projection.

8. The preassembled elongate device of claim 7, wherein the at least one protrusion is a pushbutton detent that extends through an opening in the outer tube, and wherein each of the indentations is a groove shaped to receive at least a portion of the detent.

9. The preassembled elongate device of claim 7, wherein the at least one protrusion is a tab, and wherein the plurality of axially spaced indentations is further defined as a channel having alternating axial and lateral portions defining a plurality of stop intervals, and wherein the locking mechanism is engaged and disengaged by rotation of the outer tube with respect to the inner elongate member or by rotation of the inner elongate member with respect to the outer tube.

10. The preassembled elongate device of claim 1, wherein the locking mechanism comprises:
    at least one projection that extends from the outer surface of the inner elongate member; and a plurality of axially spaced indentations disposed on the inner surface of the outer tube, wherein each of the axially spaced indentations is shaped to receive at least a portion of the at least one projection.

11. The preassembled elongate device of claim 10, wherein the at least one protrusion is a tab, and wherein the plurality of axially spaced indentations is further defined as a channel having alternating axial and lateral portions defining a plurality of stop intervals, and wherein the locking mechanism is engaged and disengaged by rotation of the outer tube with respect to the inner elongate member or by rotation of the inner elongate member with respect to the outer tube.

12. The preassembled elongate device of claim 1, wherein the locking mechanism comprises:
- a first thread of a pair of mating threads disposed on the inner surface of the outer tube;
- a second thread of the pair of mating threads disposed on the outer surface of the inner elongate member; and
- wherein the first thread matingly engages the second thread, and whereby the locking mechanism is engaged and disengaged by rotation of the outer tube with respect to the inner elongate member or by rotation of the inner elongate member with respect to the outer tube.

13. The preassembled device of claim 1, wherein the outer surface of the inner elongate member has a first proximal outer diameter and a second distal outer diameter, wherein the first proximal outer diameter is greater than the second distal outer diameter, and wherein the portion of the inner elongate member having the first proximal outer diameter does not extend beyond the annular edge of the distal end of the outer tube.

14. The preassembled device of claim 1, further comprising a sensing element located at the distal end of the inner elongate member.

15. A system, comprising:
- the preassembled device of claim 1; and
- a treatment container in fluid connection with the inner elongate member.

16. The system of claim 15, further comprising at least one therapeutic agent disposed in the treatment container for delivery into the nucleus pulposus of the intervertebral disc.

17. The system of claim 15, further comprising a sensing element located at the distal end of the inner elongate member of the preassembled device.

18. The preassembled elongate device of claim 1, wherein in the retracted position, the annular edge of the distal end of the inner elongate member is aligned with the annular edge of the distal end of the outer tube.

19. A preassembled elongate device, comprising:

an outer tube having a substantially smooth outer surface, an inner surface defining a bore within the outer tube, an open distal end having an annular edge, and a proximal end, the outer tube having a sufficient stiffness and length to penetrate skin and muscle, and wherein the annular edge of the distal end is configured to not penetrate the annulus fibrosus;

an inner elongate member housed within the bore of the outer tube, the inner elongate member having an outer surface, an inner surface defining a bore within the inner elongate member, an open distal end having an annular edge, and a proximal end, wherein the inner elongate member is slidably engaged by the outer tube such that the distal end of the inner elongate member can extend beyond the distal end of the outer tube whereby the inner elongate member has a retracted position and an extended position in relation to the outer tube, and wherein the annular edge of the distal end of the inner elongate member is configured to penetrate the annulus fibrosus and project into a nucleus pulposus of the intervertebral disc when in the extended position;

an annular plug disposed within the distal end of the outer tube and adapted to fit between the outer tube and the inner elongate member, wherein the annular plug forms a seal that prevents fluid from entering a distal end of the bore of the outer tube; and a locking mechanism configured to provide releasable frictional engagement between the outer tube and the inner elongate member, wherein the locking mechanism controls slidable movement of the inner elongate member relative to the outer tube and thereby substantially prevents movement of the inner elongate member relative to the outer tube when the locking mechanism is engaged and allows the distal end of the inner elongate member to extend beyond the distal end of the outer tube when the locking mechanism is disengaged.

* * * * *